(12) United States Patent
Gluszczak et al.

(10) Patent No.: US 8,100,562 B2
(45) Date of Patent: Jan. 24, 2012

(54) DEVICE AND SYSTEM FOR AN OPTICAL ELEMENT HOLDER

(75) Inventors: Michael Robert Gluszczak, San Jose, CA (US); Paul O. Ramstad, San Jose, CA (US); Stephen Derek Smithson, Redwood City, CA (US); George Phillips, Pacifica, CA (US); Roy W. Lindahl, Lafayette, CA (US)

(73) Assignee: Lumenis Ltd. (IL)

( * ) Notice: Subject to any disclaimer, the term of this patent is extended or adjusted under 35 U.S.C. 154(b) by 27 days.

(21) Appl. No.: 12/646,933

(22) Filed: Dec. 23, 2009

(65) Prior Publication Data
US 2010/0142206 A1 Jun. 10, 2010

Related U.S. Application Data

(63) Continuation of application No. 11/594,193, filed on Nov. 8, 2006, now Pat. No. 7,740,378.

(51) Int. Cl.
*F21V 29/00* (2006.01)
*F21V 5/00* (2006.01)

(52) U.S. Cl. ......... 362/294; 362/264; 362/580

(58) Field of Classification Search ......... 362/294, 362/264, 268, 293, 373, 455, 96, 580, 547, 362/126, 218, 345
See application file for complete search history.

(56) References Cited

U.S. PATENT DOCUMENTS

| 3,180,981 A * | 4/1965 | Ulffers ............... 362/294 |
| 3,891,311 A | 6/1975 | Fletcher et al. |
| 4,082,464 A | 4/1978 | Johnson, Jr. |
| 4,321,659 A | 3/1982 | Wheeler |
| 4,546,420 A * | 10/1985 | Wheeler et al. ....... 362/268 |
| 6,511,209 B1 | 1/2003 | Chiang |
| 6,513,962 B1 | 2/2003 | Mayshack et al. |
| 7,144,140 B2 | 12/2006 | Sun et al. |
| 2002/0105814 A1 | 8/2002 | Koren et al. |
| 2002/0136028 A1* | 9/2002 | Smith ............... 362/580 |
| 2005/0200813 A1 | 9/2005 | Kitabayashi |
| 2005/0270495 A1 | 12/2005 | Ohkubo |
| 2006/0209266 A1 | 9/2006 | Utsunomiya |

FOREIGN PATENT DOCUMENTS

| EP | 0 068 417 A1 | 1/1983 |
| EP | 1 338 236 A1 | 8/2003 |
| WO | WO 2005/096051 A1 | 10/2005 |

OTHER PUBLICATIONS

International Search Report and the Written Opinion of the International Searching Authority for counterpart PCT/US2007/023592, mailed Jul. 25, 2008.
Supplemental European Search Report of the European Searching Authority for counterpart EP 07 86 1871, mailed Dec. 21, 2009.
International Preliminary Report on Patentability for counterpart PCT/US2007/023592, mailed May 12, 2009.

* cited by examiner

*Primary Examiner* — Bao Q Truong
(74) *Attorney, Agent, or Firm* — Fogg & Powers LLC

(57) ABSTRACT

A supporting structure is disclosed for both securing optical elements for providing optimal cooling of the optical elements and the light source.

7 Claims, 5 Drawing Sheets

DEVICE AND SYSTEM FOR AN OPTICAL ELEMENT HOLDER

CROSS-REFERENCE TO RELATED APPLICATION

This application is a continuation application of U.S. patent application Ser. No. 11/594,193 filed Nov. 8, 2006, now U.S. Pat. No. 7,740,378, the entire contents of which is hereby incorporated by reference and to which priority is claimed.

BACKGROUND OF THE INVENTION

1. Field of the Invention

The present invention generally relates to a holder for an optical element. Specifically, the holder, or supporting structure is adapted for placement into a light engine for securing light filters therein. In particular, the supporting structure is adapted for both securing light filters and for providing optimal cooling for the light source and optical elements. By having embodiments of the supporting structure as described herein, a light source may operate at optimal temperatures with heretofore unrealized results.

2. Description of the Related Art

A light engine is typically used for producing and directing light having specific spectral properties onto a selected area of a patient for treatment. Often, both the intensity of the light and its particular spectral properties are selected by the treating physician. Filters and other optical elements are often used to provide the particular spectral wavelengths that the physician wants to apply to the treatment zone. These optical elements are often fragile and subject to both physical and thermal stresses. For this reason, they often have an optimal operating temperature range, and may also have a maximum operating temperature range. Similarly, the light source, which operates at temperatures as high as 370° C., also has an optimal temperature operating range. In the past, it has been difficult to maintain the operation of the light source and the filters within their optimal temperature operating ranges. There is therefore a great need in the art for a system which may include a device which allows for placement of optical elements, for example, filters, and which can also provide superior air flow for cooling the system, the light source, and the optical elements.

Accordingly, there is now provided with this invention an improved optical element supporting structure which effectively overcomes the aforementioned difficulties and longstanding problems inherent in light engine systems. These problems have been solved in a simple, convenient, and highly effective way to cool light engine systems. By having a supporting structure that provides a path for filtered light, prevents extraneous light from entering the desired light path, and providing a cooling air flow a light engine can now be operated with previously unrealized efficiency.

SUMMARY OF THE INVENTION

According to one aspect of the invention, a supporting structure for at least one optical element is disclosed. The supporting structure comprises a housing for supporting the optical element. The housing has at least one first aperture through which light may pass, and at least one second and at least one third aperture each for providing communication to the first aperture so that a cooling fluid may pass from said second aperture to and through said third aperture.

According to another aspect of an embodiment of the invention, a system for conducting light to an optical waveguide is disclosed. The system comprises a light source, a reflector for directing the light produced by the source in a path, and a structure for supporting an optical element in the light path. The structure has at least one first aperture for allowing the light to pass in the light path, and at least one second and at least one third aperture each in communication with said first aperture for allowing a cooling fluid to pass therethrough.

As will be appreciated by those persons skilled in the art, a major advantage provided by the present invention is optical elements are held in place with minimal and uniform mechanical stress or force applied to the optic. It is therefore an object of the present invention to provide cooling to both front and back surfaces of each optical element as well as to light source and in this case an optical fiber into which the light is focused. It is another object to substantially block extraneous unfiltered or untreated light from reaching the optical terminus through the cooling passage. Additional objects of the present invention will become apparent from the following description.

The method and apparatus of the present invention will be better understood by reference to the following detailed discussion of specific embodiments and the attached figures which illustrate and exemplify such embodiments.

DESCRIPTION OF THE DRAWINGS

A specific embodiment of the present invention will be described with reference to the following drawings, wherein.

DESCRIPTION OF THE PREFERRED EMBODIMENT

The following preferred embodiment as exemplified by the drawings is illustrative of the invention and is not intended to limit the invention as encompassed by the claims of this application.

The apparatus 1, as illustrated generally in FIGS. 1-9, is for holding an optical element, typically within a light engine system 2. The light engine system 2 typically has a light source which generally produces high powered unfiltered light over a wide frequency spectrum, filters the light to a preferred wavelength spectrum, and conducts the filtered light to an output, typically, to a fiber optic cable. The fiber optic cable then typically conducts the light to a Fiber Optic Illuminator attenuator and on to patient's area of treatment. A physician typically plugs an optical cable from the attenuator to the patient.

Figure 1:
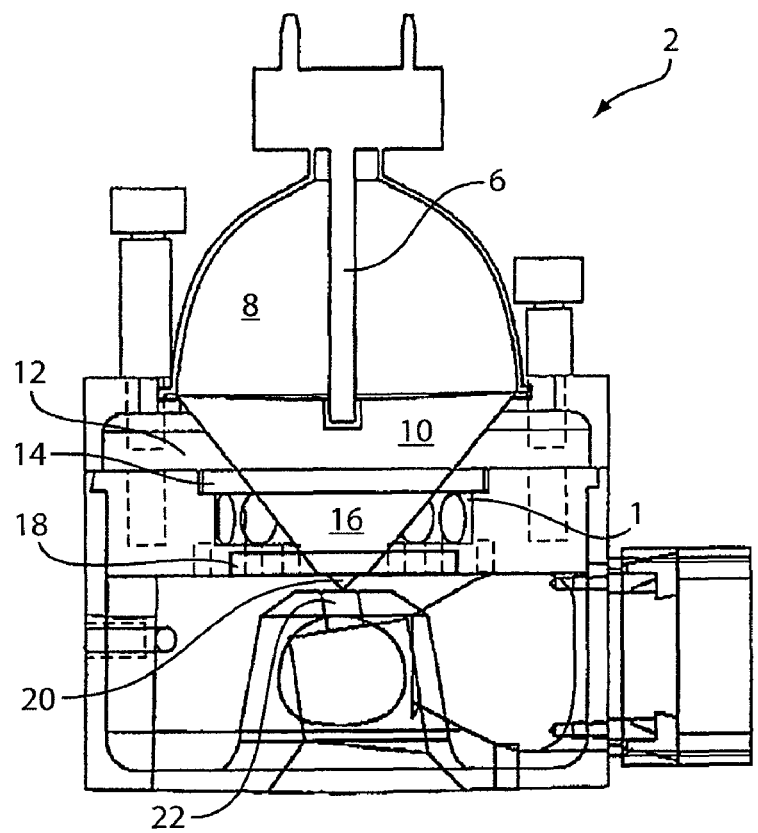
FIG. 1 is a drawing of an embodiment of a light engine system in which an embodiment of the present invention may be installed.

One embodiment of a light engine 2, as illustrated in FIG. 1, may comprise a light source 4, for example, a 50 Watt Metal Halide lamp. The light source may typically have a glass structure 6 for holding the arc and a reflector 8 surrounding the light source. The light that is produced within and reflected by the reflector 8 is typically unfiltered light. A cone of unfiltered light 10 emanates from the reflector and is directed in a path towards the optical element supporting structure 1. In this embodiment, the light source may be a lamp with a light cone. Other light sources may not have a light cone and the beam may be either collimated or diverging. Also, the light source might not be a lamp. It may alternatively be a laser, a light emitting diode, or an equivalent, as is well known to those skilled in the art. Other unfiltered light may scatter to other zones 12 of the light engine. In one embodiment of a light engine, the light may pass through a first optical element 14. The first optical element 14 may be a specific filter selected to pass a particular spectral wavelength. For example, the first optical element may be an infrared light blocking filter, such as, for example, a 3 mm thick Schott KG1 glass, or the equivalent. As is well known to those skilled in the art, this choice is but one of a multitude of choices. Alternatively, one or more optical elements of an embodiment of a light engine may also include one or more lenses, one or more gratings, one or more mirrors, for example, dichroic mirrors, one or more plane flat window glass, and/or one or more diffusers. Lenses may include, among others, both diffractive and refractive lenses.

Emanating from the first optical element 14, is a light cone of partially filtered light 16. Of course, if the particular light engine only requires a single optical element, then the light cone 16 would be the fully filtered light. As shown in the embodiment depicted in FIG. 1, the light passes onto a second optical element 18. The second optical element 18 may be the same as or different from the first optical element. For example, the second optical element may be a blue light blocking filter, such as an ultraviolet blocking filter. For example, we use 3 mm thick Schott GG435, or the equivalent. As is well known to those skilled in the art this choice is but one of a multitude of choices.

Emanating from the second optical element is a light cone of fully filtered light 20. Of course, if the particular light engine requires still more light filtering, then subsequent optical elements may be used by stacking further optical element supporting structures 1. The light may then pass through multiple filters held by multiple optical elements. In this case, although the light path would preferably be in series, the air path therethrough (discussed below) would preferably be in parallel. The exiting fully filtered light would then be directed into an entrance port of an optical fiber 22. In this embodiment, both filters are parallel to each other and at normal incidence to the optical axis. In other embodiments, the filters need not be parallel to each other or at normal incidence to the optical axis.

Figure 2:
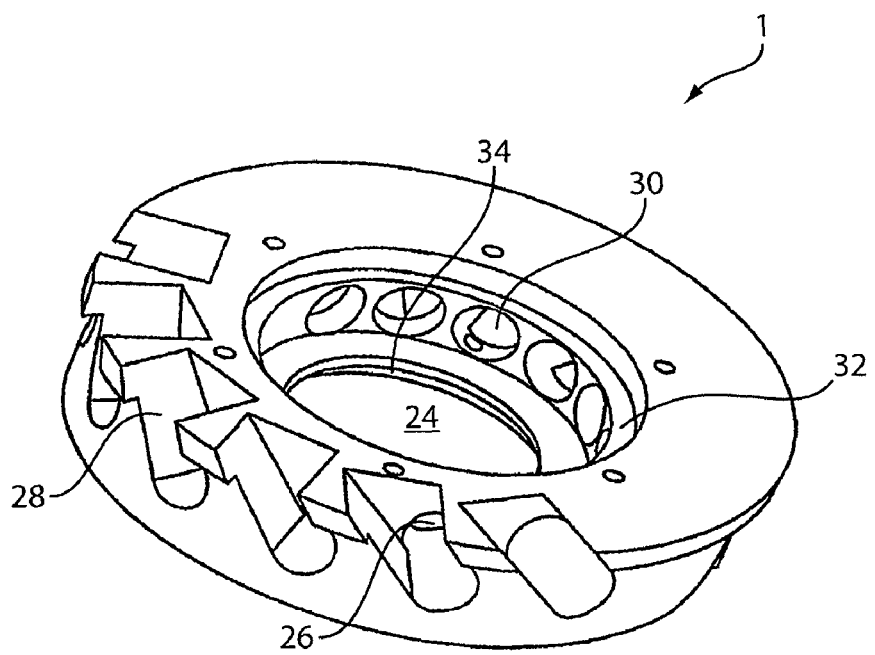
FIG. 2 is an isometric view of an embodiment of the present invention.

FIG. 2 illustrates an isometric view of an embodiment of a supporting structure 1 of at least one optical element. The optical element holder or supporting structure 1 may be manufactured of a wide variety of materials including metal, for example, stainless steel, high impact heat resistant plastic, glass, or ceramic, etc. as is well known to those skilled in the art. The supporting structure may be either molded or machined. The embodiments of the supporting structure described herein preferably have several main purposes. The first is to securely hold the optical elements in the light path of the light engine without inducing unnecessary physical stress or strain.

Another main purpose of the supporting structure may be to allow a cooling medium to pass across at least one surface of each optical element for reducing thermal stress of the optical element. One embodiment of the present invention may use air as the cooling medium. Other embodiments of the present invention may use a wide variety of substances as the cooling media, for example, a liquid or a gas. Still another main purpose of the optical element supporting structure may include at least partially preventing unwanted unfiltered light transmission to the exit of the engine.

Typically, the light source of the glass arc has optimal operating temperature ranges, for example, from about 200° C. to about 285° C., and preferably about 220° C. The use of an embodiment of the supporting structure will allow use of the light engine within temperature operating guidelines and will help to prevent breaking optical elements due to thermal stress even if the system fan is turned off.

As shown in FIG. 2, an embodiment of a supporting structure 1 has a central aperture 24. Light passes through the central aperture 24. Although the supporting structure I depicted in FIG. 2 is toroidal, any shape may be used to support an optical element. On a side of the supporting structure is at least one second aperture 26. The second aperture provides communication, typically air flow, from outside the supporting structure 1 to the central aperture 24. Thus, air passage is provided from outside the supporting structure into the central aperture 24 through at least one second aperture 26. As shown, a plurality of second apertures 26 are preferable.

The second aperture 26 has an entrance port 28. The entrance port is configured to provide a directed flow of air through the aperture 26. The entrance port is preferably configured to be at an angle, for example, 45°, although entrance ports using other angles may also be used. Forming the entrance port at an angle has been found to provide improved air circulation and cooling to the optical elements. Having the entrance port at an angle also provides for light baffling as explained below.

Figure 4:
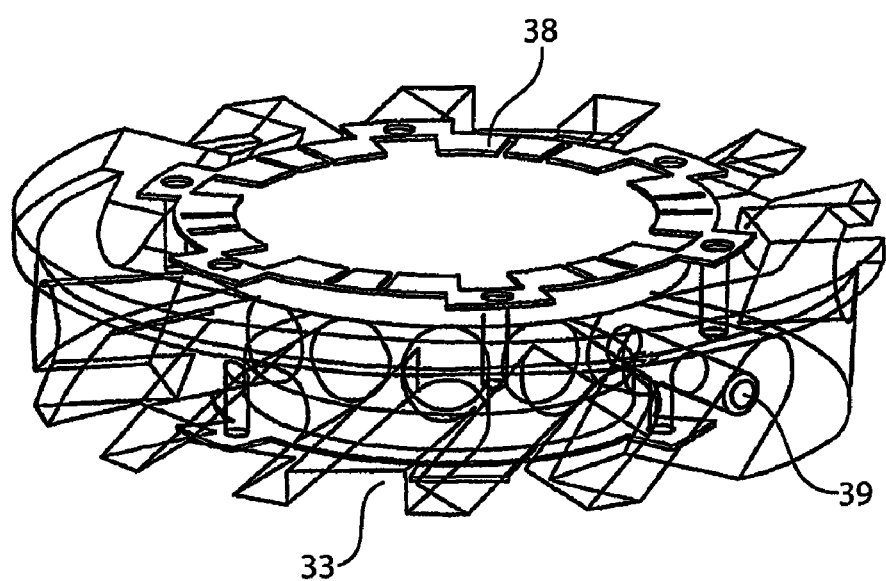
FIG. 4 is a transparent isometric view of an embodiment of the present invention.
Figure 5:
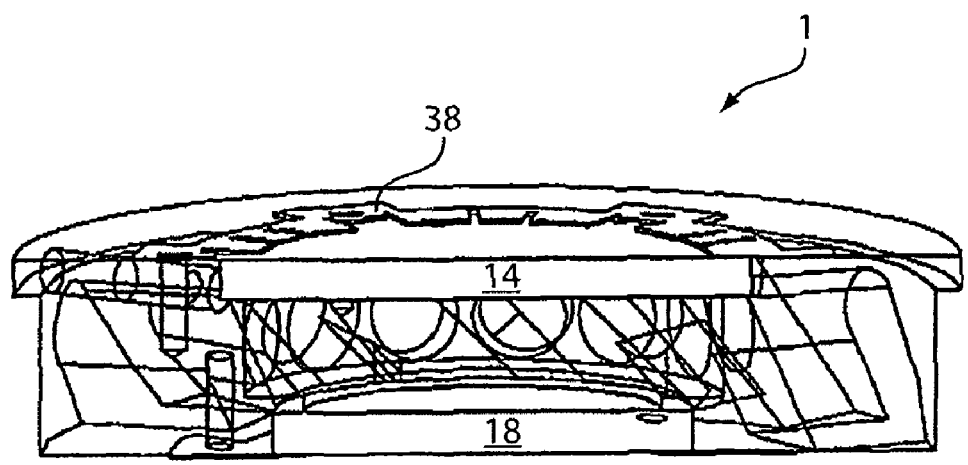
FIG. 5 is another transparent isometric view of an embodiment of the present invention.

As further shown in FIG. 2, an embodiment of a supporting structure 1 has at least one third aperture 30 on a side opposite that of the side having the second aperture. The third aperture provides communication, typically air flow, from the central aperture 24 to outside the supporting structure 1. Thus, air passage is provided from outside the supporting structure into the central aperture 24 through at least one second aperture 26 and out of the central aperture through at least one third aperture. As shown, a plurality of third apertures 30 are preferable. An exit port 33 of the third aperture is shown in FIG. 4. The exit port 33 is preferably configured at an angle, for example, 45°, although exit ports may have other angles as well.

Figure 3:
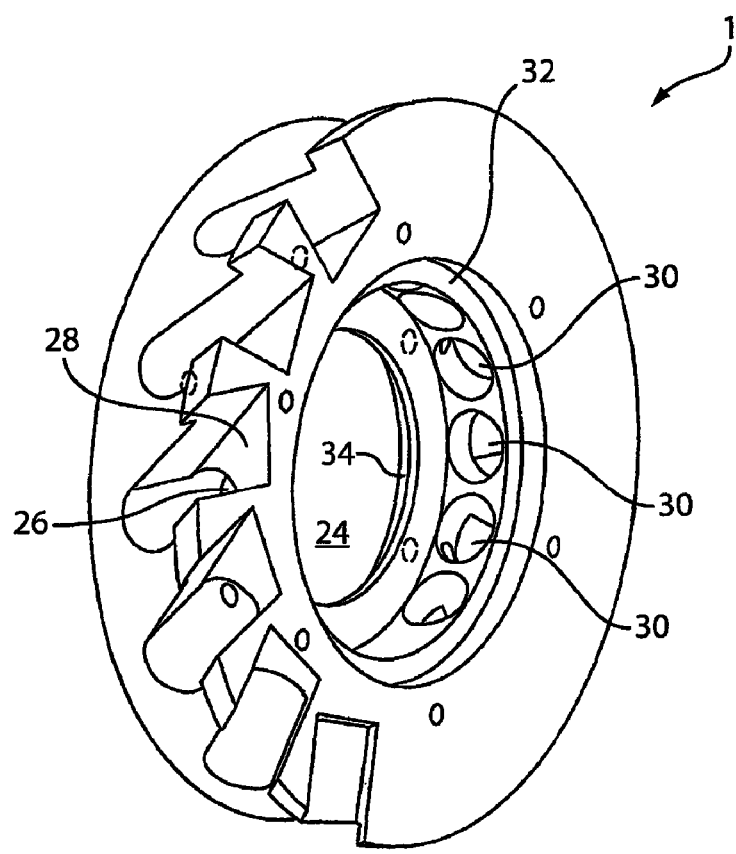
FIG. 3 is another isometric view of an embodiment of the present invention.

As shown in FIGS. 2 and 3, an optical element seat 32 is provided for seating an optical element on one side of the central aperture. Although the seat 32 for the optical element is depicted in the illustrated embodiments as a recess, any suitable optical positioning member may be used, for example, a shoulder, a frame, etc. as is well known to those skilled in the art. If a second optical element is used, it is preferable to include a second seat 34 for the second optical element. Surrounding each seat, on a face of the supporting structure are positions to be used for securing the optical elements to the supporting structure.

As more particularly shown in FIG. 4, a retainer 38, which may be in the form of a ring, may preferably be used to secure the optical elements to the supporting structure. The ring may be rigid, may be made of spring material, but of course, as is well known to those skilled in the art, any form of retaining mechanism including adhesives may be used, for securing an optical element to a supporting structure. The preferred retainer ring means is made of copper alloy, with a multi-fingered radial pattern of elements in contact with and securing each of the optical elements. These rings may be, in turn, secured to the optical element holder in a plurality of locations around its periphery. Also shown in FIG. 4 is a pin 39 which may preferably be attached to the supporting structure. The pin 39 is for orienting the supporting structure relative to the path in which the air flows. It is preferable to orient the supporting structure so that the second and third apertures are substantially aligned in the path that the air flows as it flows from the side opposite the exhaust fans to the side on which the exhaust fans are located (as more particularly shown in path 44 of FIG. 7, discussed below).

Figure 6:
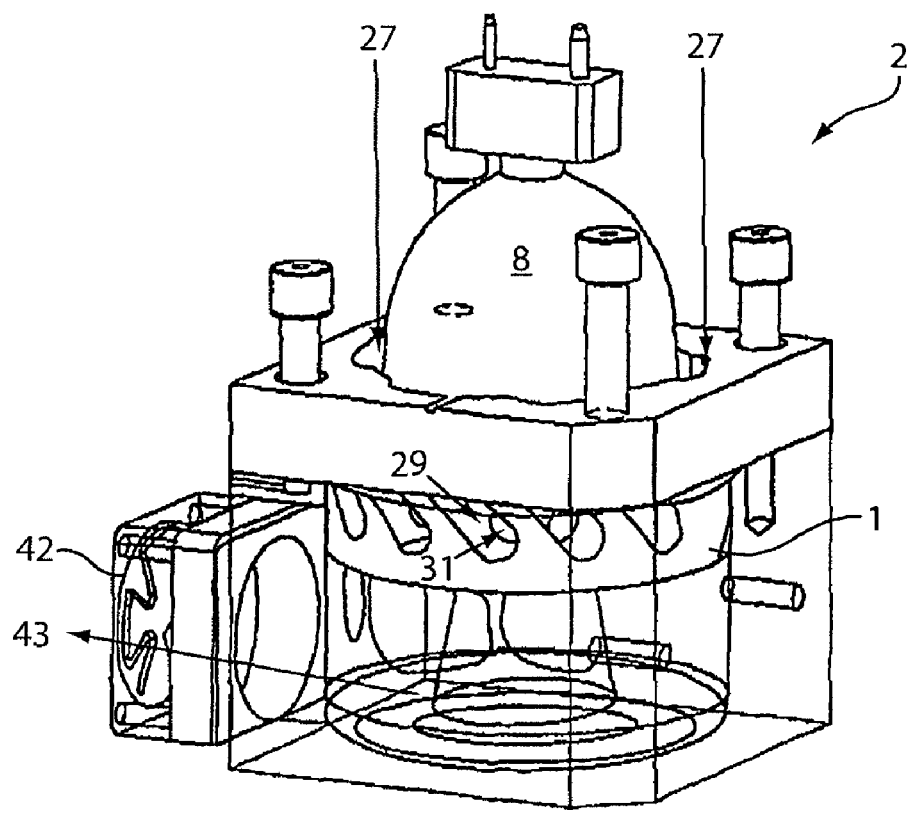
FIG. 6 is a transparent isometric view of an embodiment of a light engine showing the air flow through an embodiment of the present invention.

FIG. 6 illustrates the path of the cooling fluid, in this embodiment, air, through the light engine as provided by an embodiment of the supporting structure of the present invention. Air enters through passages on the outside circumference of the reflector 8. The air is drawn into at least one void 27 peripheral to the outside of the entrance port 28 of the second aperture 26. The air then passes into the entrance port, as shown by arrow 29, through the second aperture 26, as shown by arrow 31, into the central aperture 24. The central aperture is shown in this embodiment sealed on either side by optical elements. The air then passes out of the central aperture through the third aperture and into a cavity 40. The cavity 40 acts as an intake plenum to at least one exhaust fan 42, and preferably two. The draft of air flow results in a swirling of turbulent air around the light source thereby providing cooling thereto. The flow of air through the supporting structure also provides cooling to the optical elements. The air then exits the light engine through the exhaust fans 42 as shown by arrow 43.

Figure 7:
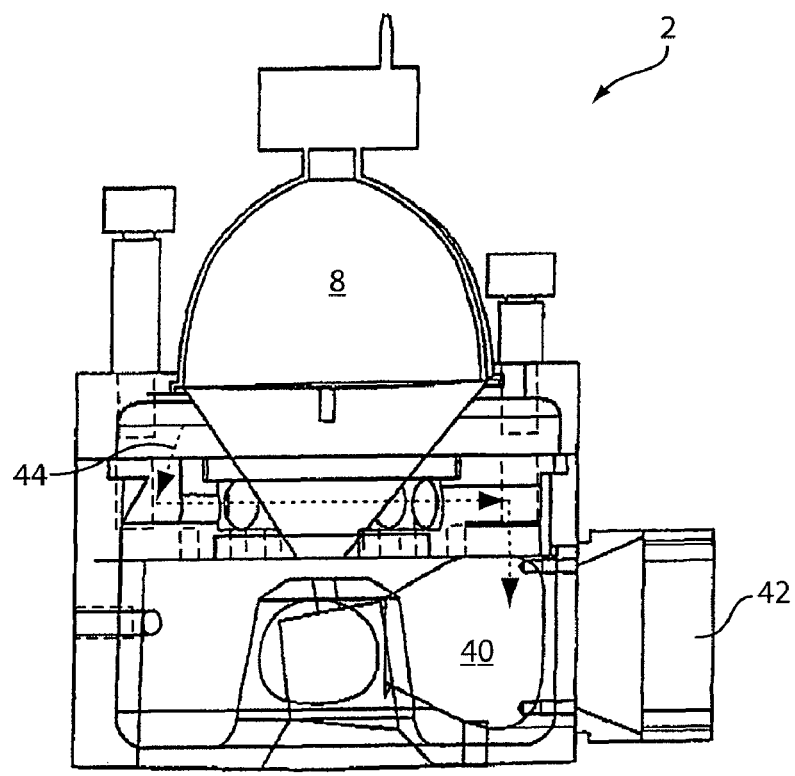
FIG. 7 is a transparent isometric view of an embodiment of a light engine showing the light path through an embodiment of the present invention.

FIG. 7 illustrates the path 44 of the stray or undirected light. Undirected or stray light would have to take essentially the same or similar path as the path of the air flow. Since this is a serpentine path, every turn decreases the opportunity for the unfiltered light to interfere with the directed filtered light path. By providing light baffling of undesired wavelengths of light, only the filtered light may enter the entrance port of the optical fiber 22 and onto the patient. This is especially important if the light is to be conducted to the patient's eye. The spectral content of light that is conducted to the eye is of great concern and damage due to UV and blue light, referred in the technical literature as blue toxicity, should be avoided. As is well known to those skilled in the art, IR wavelengths should also be avoided for thermal reasons.

As shown in FIG. 7, the entrance port to the optical fiber 22 is preferably at an angle to further diminish the chance of interference. Having the port of the optical fiber at an angle also diminishes the chance of light reflecting back onto the lamp arc which would reduce its life.

Figure 8:
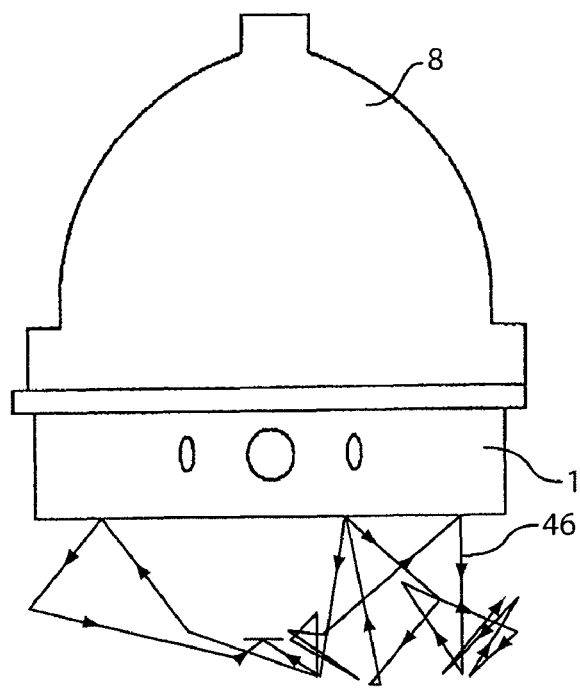
FIG. 8 is an illustration showing how light rays are prevented from proceeding beyond an embodiment of the present invention.

As more particularly shown in FIG. 8, unwanted light rays 46 are prevented from proceeding beyond an embodiment of the present invention. The combined benefit of a plurality of angled entrance (at least one $2^{nd}$ aperture) and exit (at least one $3^{rd}$ aperture) ports located on opposite sides of the optical element holder is graphically illustrated in this figure. In a preferred embodiment, unfiltered light energy may be reduced by about 3 orders of magnitude. Having unwanted rays enter through cavity 40 may be a concern in some cases, but not in this case because the amount is so small. In all cases unfiltered light is substantially prevented from exiting the lamp. Certain wavelength regions of light from lamps, Ultra-Violet for example, are harmful and should be avoided. The entrance port for air, for example, may be the only place for unfiltered light to exit the Light Engine. It has been found that the measured amount is much less than the energy typically emitted from overhead fluorescent room lights. Some unfiltered light from scattered light that may exit through the light engine system may conceivably exit through the fan but this amount is substantially less than what exits the coolant entrance.

Figure 9:
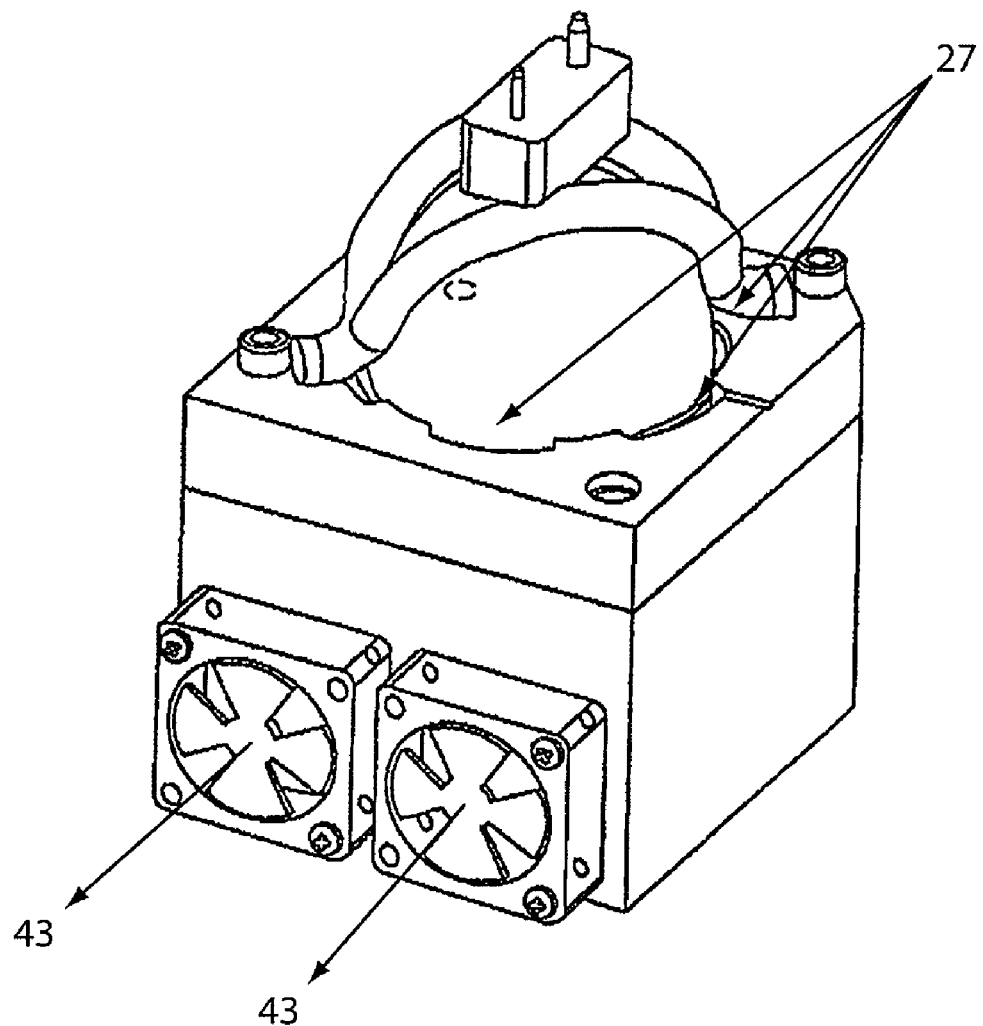
FIG. 9 is an external isometric view of an embodiment of a light engine.

FIG. 9 is an external isometric view of an embodiment of a light engine. The void located on the periphery of the reflector 27 is shown along with the fans on the exterior of the light engine.

Although the particular embodiments shown and described above will prove to be useful in many applications in the optical arts to which the present invention pertains, further modifications of the present invention will occur to persons skilled in the art. All such modifications are deemed to be within the scope and spirit of the present invention as defined by the appended claims.

What is claimed is:

1. A system for supporting and cooling, comprising:
    a. a housing;
    b. a light source;
    c. a reflector for directing the light produced by the source along an optical path;
    d. a torodial structure downstream of the reflector having a first central aperture in the opening of the torodial structure through which light produced by the light source along the optical path passes through; and
    e. a pluarality of second apertures formed around the outside periphery of the torodial structure and piercing through to the inner periphery of the torodial structure, the second apertures being at angles other than perpendicular to the outside periphery of the torodial structure, the second angled apertures causing cooling fluid to swirl across the first central aperture to cool the light source.

2. The system of claim 1, further including a structure for supporting one or more optical elements.

3. The system of claim 2, wherein said optical element is a single filter.

4. The system of claim 2, wherein the at least one optical element includes one or more of: a filter, a lens; an optical mirror, a grating, a dichroic mirror, a flat plane glass, and a diffuser.

5. The system of claim 1, wherein the cooling fluid is one or more of: a gas and a liquid medium.

6. The system of claim 1, wherein the second apertures are at about 45 degrees to the outer periphery of the torodial structure.

7. The system of claim 1, further comprising:
    at least one fan downstream of the torodial structure to cause the cooling fluid to move through the torodial structure, across the central aperture, and through the fan.

* * * * *